US012582385B2

(12) United States Patent　　　　(10) Patent No.: US 12,582,385 B2
Wang et al.　　　　　　　　　　　(45) Date of Patent: Mar. 24, 2026

(54) SYSTEMS AND METHODS FOR ULTRASOUND IMAGING

(71) Applicant: WUHAN UNITED IMAGING HEALTHCARE CO., LTD., Wuhan (CN)

(72) Inventors: Ruojin Wang, Wuhan (CN); Li Cheng, Wuhan (CN); Hao Zhu, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 147 days.

(21) Appl. No.: 18/401,237

(22) Filed: Dec. 29, 2023

(65) Prior Publication Data

US 2024/0215953 A1　　Jul. 4, 2024

(30) Foreign Application Priority Data

Dec. 29, 2022　(CN) .......................... 202211708239.5

(51) Int. Cl.
*A61B 8/00*　　　(2006.01)

(52) U.S. Cl.
CPC ................ *A61B 8/465* (2013.01); *A61B 8/54* (2013.01)

(58) Field of Classification Search
CPC ......... A61B 8/465; A61B 8/54; A61B 8/4477; A61B 8/4427; A61B 8/08
See application file for complete search history.

(56) References Cited

U.S. PATENT DOCUMENTS

| 2003/0097065 A1 | 5/2003 | Lee et al. |
| 2012/0157843 A1 | 6/2012 | Lavin et al. |
| 2012/0226161 A1* | 9/2012 | Pelissier ................ A61B 8/467 600/443 |
| 2015/0301712 A1* | 10/2015 | Ban ..................... G06F 3/04842 715/765 |
| 2019/0033435 A1* | 1/2019 | Sakai ................... G01S 7/52025 |
| 2019/0383920 A1 | 12/2019 | Kook et al. |
| 2021/0353260 A1* | 11/2021 | Srinivasa Naidu ......................... G01S 7/52085 |

(Continued)

FOREIGN PATENT DOCUMENTS

| CN | 102440803 A | 5/2012 |
| CN | 111317501 A | 6/2020 |
| CN | 114047988 A | 2/2022 |

(Continued)

OTHER PUBLICATIONS

The Extended European Search Report in European Application No. 23220633.4 mailed on Jun. 17, 2024, 9 pages.

(Continued)

*Primary Examiner* — Kaitlyn E Sebastian
(74) *Attorney, Agent, or Firm* — METIS IP LLC

(57) ABSTRACT

Systems and methods for ultrasound imaging are provided. The systems may determine a target clinical scene associated with a target subject. The systems may determine, based on a corresponding relationship between clinical scenes and ultrasound probes, at least one ultrasound probe corresponding to the target clinical scene and determine a target ultrasound probe from the at least one ultrasound probe. The systems may generate an ultrasound image of the target subject by performing the ultrasound imaging using the target ultrasound probe.

18 Claims, 9 Drawing Sheets

(56)               References Cited

U.S. PATENT DOCUMENTS

2022/0296219 A1 *   9/2022  Aladahalli ............. A61B 8/469

FOREIGN PATENT DOCUMENTS

| CN | 116264972 A | * | 6/2023 | ........... A61B 8/4477 |
| JP | 2015181900 A | * | 10/2015 | ............. A61B 8/467 |
| WO | 2020024255 A1 | | 2/2020 | |

OTHER PUBLICATIONS

First Office Action in Chinese Application No. 202211708239.5
mailed on May 14, 2025, 15 pages.

* cited by examiner

<u>100</u>

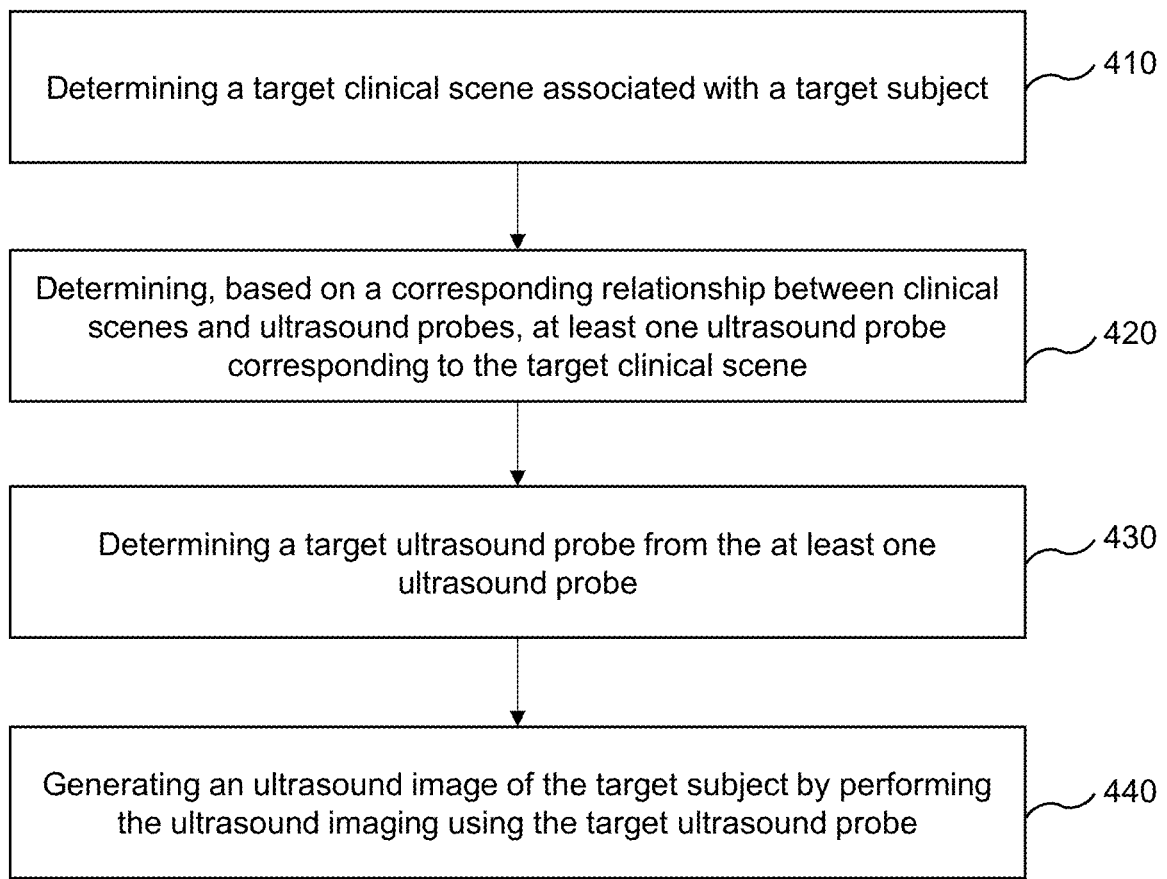

400

Determining a target clinical scene associated with a target subject — 410

Determining, based on a corresponding relationship between clinical scenes and ultrasound probes, at least one ultrasound probe corresponding to the target clinical scene — 420

Determining a target ultrasound probe from the at least one ultrasound probe — 430

Generating an ultrasound image of the target subject by performing the ultrasound imaging using the target ultrasound probe — 440

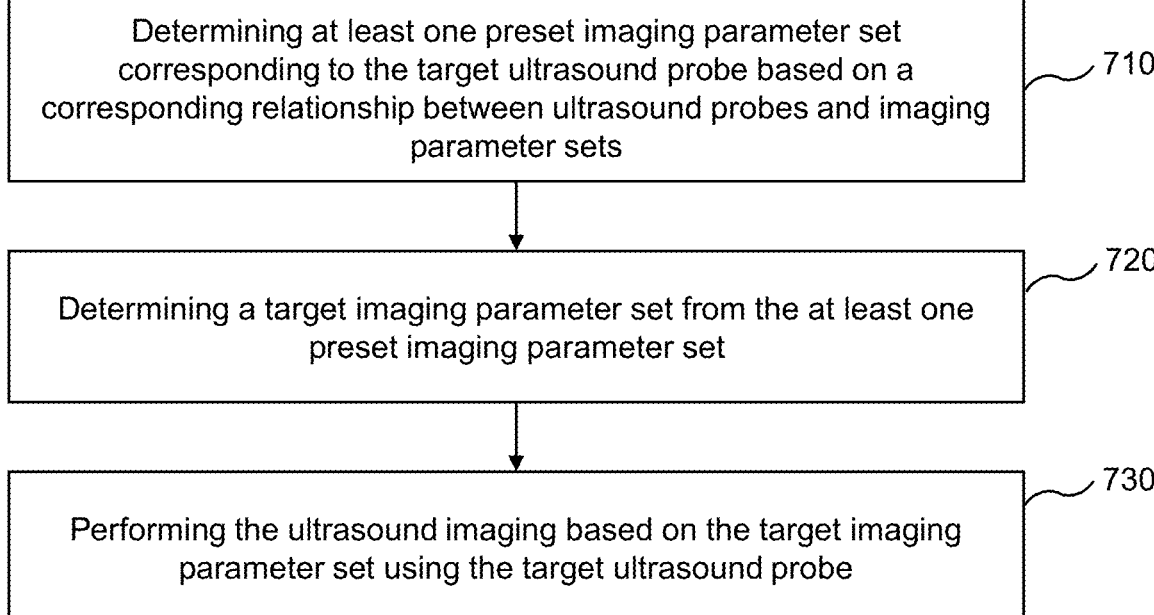

Determining at least one preset imaging parameter set corresponding to the target ultrasound probe based on a corresponding relationship between ultrasound probes and imaging parameter sets — 710

Determining a target imaging parameter set from the at least one preset imaging parameter set — 720

Performing the ultrasound imaging based on the target imaging parameter set using the target ultrasound probe — 730

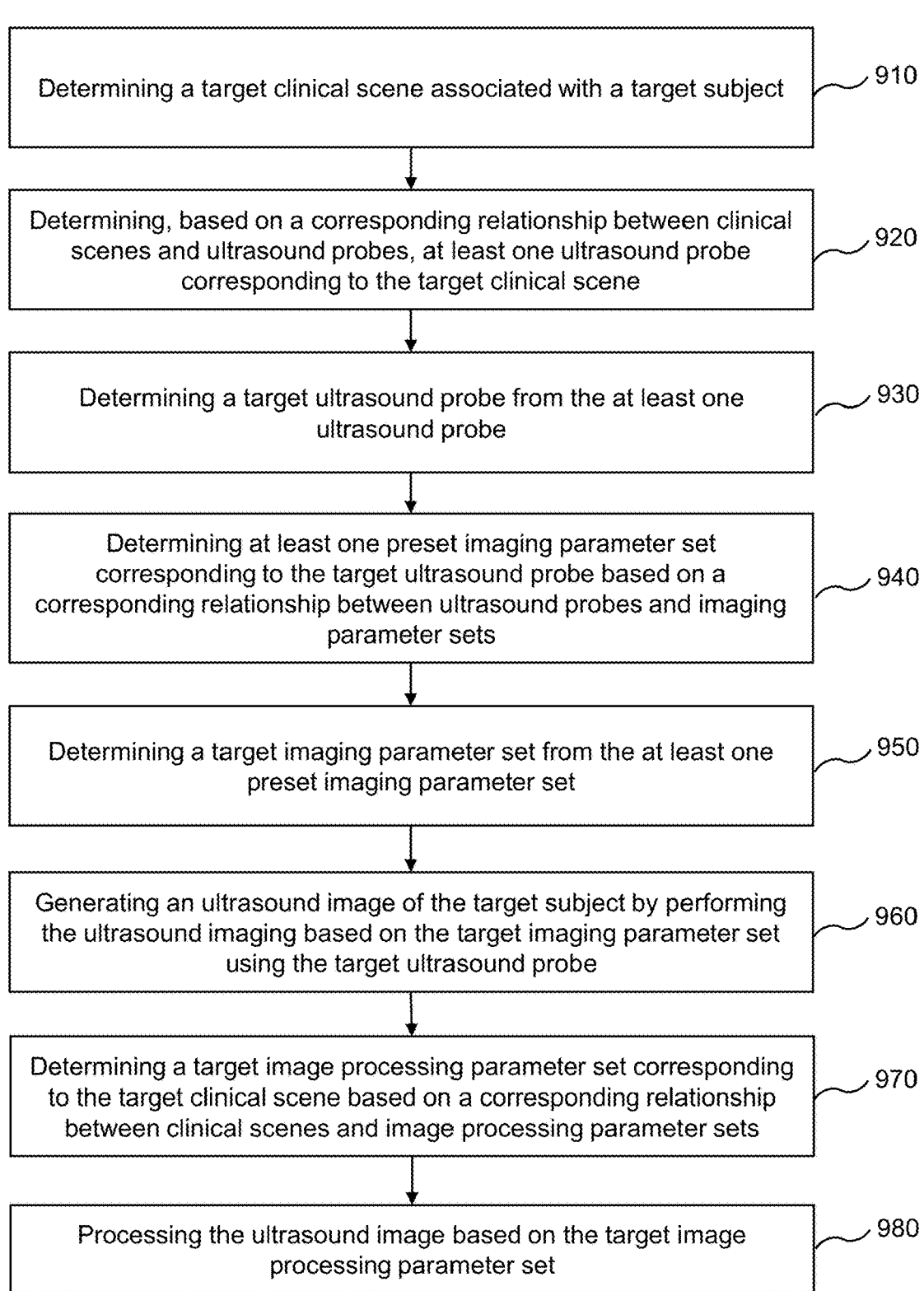

Determining a target clinical scene associated with a target subject — 910

Determining, based on a corresponding relationship between clinical scenes and ultrasound probes, at least one ultrasound probe corresponding to the target clinical scene — 920

Determining a target ultrasound probe from the at least one ultrasound probe — 930

Determining at least one preset imaging parameter set corresponding to the target ultrasound probe based on a corresponding relationship between ultrasound probes and imaging parameter sets — 940

Determining a target imaging parameter set from the at least one preset imaging parameter set — 950

Generating an ultrasound image of the target subject by performing the ultrasound imaging based on the target imaging parameter set using the target ultrasound probe — 960

Determining a target image processing parameter set corresponding to the target clinical scene based on a corresponding relationship between clinical scenes and image processing parameter sets — 970

Processing the ultrasound image based on the target image processing parameter set — 980

FIG. 9

SYSTEMS AND METHODS FOR ULTRASOUND IMAGING

CROSS-REFERENCE TO RELATED APPLICATIONS

This application claims priority to Chinese Patent Application No. 202211708239.5 filed on Dec. 29, 2022, the entire contents of which are hereby incorporated by reference.

TECHNICAL FIELD

The present disclosure generally relates to medical imaging, and more particularly, relates to systems and methods for ultrasound imaging.

BACKGROUND

Ultrasound imaging is a technology that uses ultrasound waves to generate an ultrasound image of internal tissues, blood flow, etc. of a target subject. Ultrasound imaging is widely used in the field of medical imaging because it is non-invasive and brings no radiation. However, the operating efficiency of ultrasonic imaging in the existing technology is low.

SUMMARY

An aspect of the present disclosure relates to a method for ultrasound imaging. The method is implemented on a computing device including at least one processor and at least one storage device. The method may include determining a target clinical scene associated with a target subject. The method may include determining, based on a corresponding relationship between clinical scenes and ultrasound probes, at least one ultrasound probe corresponding to the target clinical scene and determining a target ultrasound probe from the at least one ultrasound probe. The method may further include generating an ultrasound image of the target subject by performing the ultrasound imaging using the target ultrasound probe.

In some embodiments, determining the target clinical scene associated with the target subject includes obtaining first feature information of the target subject, the first feature information being related to the examination need and/or physical characteristics of the target subject; and determining the target clinical scene based on the first feature information.

In some embodiments, determining the target clinical scene based on the first feature information includes obtaining second feature information of an operator of the ultrasound imaging, the second feature information being related to the department and/or the preference of the operator; and determining the target clinical scene based on the first feature information and the second feature information.

In some embodiments, determining the target clinical scene associated with the target subject includes displaying multiple preset clinical scenes via a user terminal communicatively connected to the computing device; receiving, via the user terminal, a first trigger instruction for selecting one preset clinical scene from the multiple preset clinical scenes; and designating the selected preset clinical scene as the target clinical scene.

In some embodiments, visual elements representing the multiple preset clinical scenes are displayed on the user terminal, and an arrangement of the visual elements on the user terminal is determined based on second feature information of an operator of the ultrasound imaging.

In some embodiments, visual elements representing the multiple preset clinical scenes are displayed on the user terminal, and each of the visual elements includes an icon representing a scanning part of the corresponding preset clinical scene.

In some embodiments, a body model representing the target subject is displayed on the user terminal, and the body model includes multiple scanning parts representing the multiple preset clinical scenes.

In some embodiments, when the at least one ultrasound probe corresponding to the target clinical scene includes multiple ultrasound probes, the determining a target ultrasound probe includes actuating one ultrasound probe among the multiple ultrasound probes; and designating the actuated ultrasound probe as the target ultrasound probe.

In some embodiments, the actuated ultrasound probe is selected based on a ranking result of the multiple ultrasound probes, and the ranking result of the multiple ultrasound probes is determined based on at least one of a usage frequency of each of the multiple ultrasound probes, a last usage time of each of the multiple ultrasound probes, or a fault record of each of the multiple ultrasound probes.

In some embodiments, the actuated ultrasound probe is selected from the multiple ultrasound probes based on first feature information of the target subject and/or second feature information of an operator using a first machine learning model.

In some embodiments, when the at least one ultrasound probe corresponding to the target clinical scene includes multiple ultrasound probes, the determining the target ultrasound probe from the at least one ultrasound probe includes displaying the multiple ultrasound probes via a user terminal communicatively connected to the computing device; receiving, via the user terminal, a second trigger instruction for selecting one ultrasound probe from the multiple ultrasound probes; and designating the selected ultrasound probe as the target ultrasound probe.

In some embodiments, the performing the ultrasound imaging using the target ultrasound probe further includes determining at least one preset imaging parameter set corresponding to the target ultrasound probe based on a corresponding relationship between ultrasound probes and imaging parameter sets; determining a target imaging parameter set from the at least one preset imaging parameter set; and performing the ultrasound imaging based on the target imaging parameter set using the target ultrasound probe.

In some embodiments, when the at least one preset imaging parameter set corresponding to the target ultrasound probe includes multiple preset imaging parameter sets, the determining a target imaging parameter set includes actuating one preset imaging parameter set among the multiple preset imaging parameter sets; and designating the actuated preset imaging parameter set as the target imaging parameter set.

In some embodiments, the actuated preset imaging parameter set is selected based on a ranking result of the multiple preset imaging parameter sets, and the ranking result of the multiple preset imaging parameter sets is determined based on at least one of a usage frequency of each of the multiple preset imaging parameter sets, a last usage time of each of the multiple preset imaging parameter sets, or a fault record associated with a usage of each of the multiple preset imaging parameter sets.

In some embodiments, the actuated preset imaging parameter set is selected from the multiple preset imaging parameter sets based on first feature information of the target subject and/or second feature information of an operator using a second machine learning model.

In some embodiments, when the at least one preset imaging parameter set corresponding to the target ultrasound probe includes multiple preset imaging parameter sets, determining the target imaging parameter set from the at least one preset imaging parameter set includes displaying the multiple preset imaging parameter sets via a user terminal communicatively connected to the computing device; receiving, via the user terminal, a third trigger instruction for selecting one preset imaging parameter set from the multiple preset imaging parameter sets; and designating the selected preset imaging parameter set as the target imaging parameter set.

In some embodiments, the method further includes determining a target image processing parameter set corresponding to the target clinical scene based on a corresponding relationship between clinical scenes and image processing parameter sets; and processing the ultrasound image based on the target image processing parameter set.

Another aspect of the present disclosure relates to a system for ultrasound imaging. The system includes at least one storage device including a set of instructions and at least one processor in communication with the at least one storage device. When executing the set of instructions, the at least one processor is directed to cause the system to implement operations. The operations may include determining a target clinical scene associated with a target subject. The operations may include determining, based on a corresponding relationship between clinical scenes and ultrasound probes, at least one ultrasound probe corresponding to the target clinical scene and determining a target ultrasound probe from the at least one ultrasound probe. The operations may further include generating an ultrasound image of the target subject by performing the ultrasound imaging using the target ultrasound probe.

A still further aspect of the present disclosure relates to a non-transitory computer readable medium including executable instructions. When the executable instructions are executed by at least one processor, the executable instructions direct the at least one processor to perform a method. The method may include determining a target clinical scene associated with a target subject. The method may include determining, based on a corresponding relationship between clinical scenes and ultrasound probes, at least one ultrasound probe corresponding to the target clinical scene and determining a target ultrasound probe from the at least one ultrasound probe. The method may further include generating an ultrasound image of the target subject by performing the ultrasound imaging using the target ultrasound probe.

Additional features may be set forth in part in the description which follows, and in part may become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 4 is a flowchart illustrating an exemplary ultrasound imaging process according to some embodiments of the present disclosure;

FIG. 7 is a flowchart illustrating an exemplary ultrasound imaging process according to some embodiments of the present disclosure;

FIG. 9 is a flowchart illustrating an exemplary ultrasound imaging process according to some embodiments of the present disclosure.

DETAILED DESCRIPTION

Figure 1:
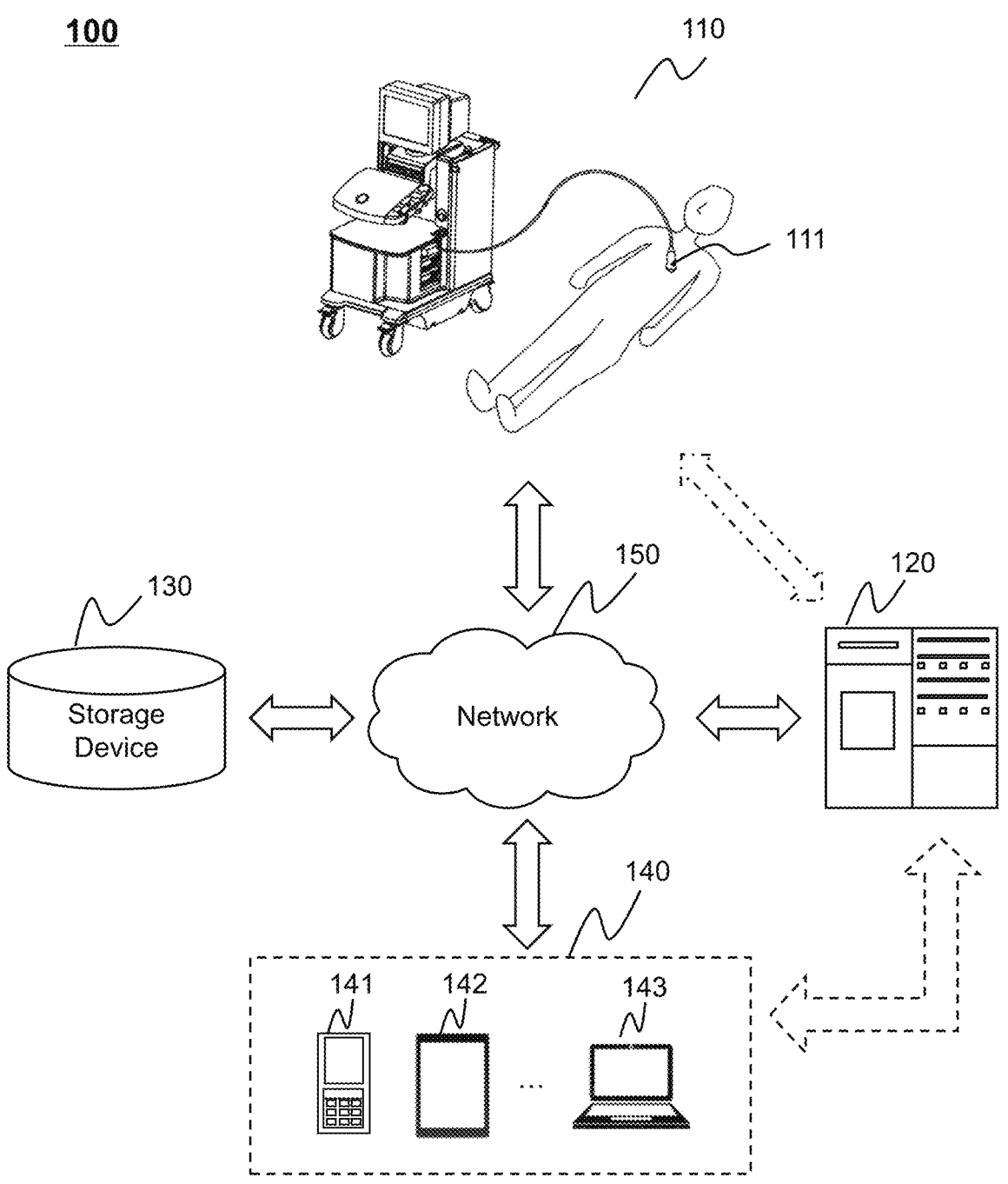
FIG. 1 is a schematic diagram illustrating an exemplary ultrasound imaging system according to some embodiments of the present disclosure.

In the following detailed description, numerous specific details may be set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments may be readily apparent to those skilled in the art, and the general principles defined herein may be applied to other embodiments and applications without departing from the spirit and scope of the present disclosure. Thus, the present disclosure may be not limited to the embodiments shown, but to be accorded the widest scope consistent with the claims.

The terminology used herein may be for the purpose of describing particular example embodiments only and may be not intended to be limiting. As used herein, the singular forms "a," "an," and "the" may be intended to include the plural forms as well, unless the context clearly indicates otherwise. It may be understood that the terms "system," "unit," "module," and/or "block" used herein are one method to distinguish different components, elements, parts, sections or assemblies of different levels in ascending order. However, the terms may be displaced by another expression if they achieve the same purpose.

The modules (or units, blocks, units) described in the present disclosure may be implemented as software and/or hardware modules and may be stored in any type of non-transitory computer-readable medium or other storage devices. In some embodiments, a software module may be compiled and linked into an executable program. It may be appreciated that software modules may be callable from other modules or from themselves, and/or may be invoked in response to detected events or interrupts. Software modules configured for execution on computing devices may be provided on a computer readable medium or as a digital download (and can be originally stored in a compressed or installable format that requires installation, decompression, or decryption prior to execution). Such software code may be stored, partially or fully, on a memory device of the executing computing device, for execution by the computing device. Software instructions may be embedded in a firmware, such as an Erasable Programmable Read-Only Memory (EPROM). It may be further appreciated that hardware modules (e.g., circuits) may be included in connected or coupled logic units, such as gates and flip-flops, and/or may be included in programmable units, such as programmable gate arrays or processors. The modules or computing device functionality described herein may be preferably implemented as hardware modules, but may be software modules as well. In general, the modules described herein refer to logical modules that may be combined with other modules or divided into units despite their physical organization or storage.

Certain terminology has been used to describe embodiments of the present disclosure. For example, the terms "one embodiment," "an embodiment," and/or "some embodiments" may mean that a particular feature, structure, or characteristic described in connection with the embodiment is in at least one embodiment of the present disclosure. Therefore, it is emphasized and should be appreciated that two or more references to "an embodiment" or "one embodiment" or "an alternative embodiment" in various portions of this specification may not necessarily all referring to the same embodiment. Furthermore, the particular features, structures or characteristics may be combined as suitable in one or more embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings may be for the purpose of illustration and description only and may be not intended to limit the scope of the present disclosure.

The flowcharts used in the present disclosure may illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Generally, during the ultrasound imaging process, an operator (e.g., a doctor) needs to manually select an ultrasound probe, an imaging parameter set, etc. for performing the ultrasound imaging. After the ultrasound image is generated, the operator further needs to select a measurement package, an annotation library, a report template to analyze and annotate the generated ultrasound image, and generate a report of the ultrasound imaging. These operations make display interface, operating buttons, and operating functions of the ultrasound imaging device very complicated, which is not conducive to new operators getting started quickly and increases the operator's burden.

The present disclosure provides systems and methods for ultrasound imaging. The systems may determine a target clinical scene associated with a target subject. The target clinical scene may be related to an examination need of the target subject. Based on a corresponding relationship between clinical scenes and ultrasound probes, the systems may determine at least one ultrasound probe corresponding to the target clinical scene and determine a target ultrasound probe from the at least one ultrasound probe. Further, in some embodiments, based on a corresponding relationship between ultrasound probes and imaging parameter sets, the systems may determine at least one preset imaging parameter set corresponding to the target ultrasound probe and determine a target imaging parameter set from the at least one preset imaging parameter set. Based on the target imaging parameter set, the systems may generate an ultrasound image of the target subject by performing the ultrasound imaging using the target ultrasound probe. In addition, based on a corresponding relationship between clinical scenes and image processing parameter sets, the systems may determine a target image processing parameter set (e.g., the measurement package, the annotation library, the report template) corresponding to the target clinical scene and process the ultrasound image based on the target image processing parameter set.

According to the embodiments of the present disclosure, after the target clinical scene is determined, the target ultrasound probe, the target imaging parameter set, and/or the target image processing parameter set can be automatically determined based on the target clinical scene, which eliminates the need for the operator to manually set the ultrasound probe, the corresponding imaging parameter set, and the corresponding image processing parameter set, thereby simplifying the display interface, operating buttons, and/or operating functions of the ultrasound imaging device, and accordingly, improving the convenience, standardization, and efficiency of the ultrasound imaging. In addition, the imaging process is user-friendly and can be easily performed by operators (including inexperienced operators), thereby making the ultrasound imaging systems and methods provided in the embodiments of the present disclosure highly practical.

FIG. 1 is a schematic diagram illustrating an ultrasound imaging system 100 according to some embodiments of the present disclosure. As shown in FIG. 1, the ultrasound imaging system 100 may include an ultrasound imaging device 110, a processing device 120, a storage device 130, one or more user terminals 140, and a network 150. In some embodiments, the ultrasound imaging device 110, the processing device 120, the storage device 130, and/or the user terminal(s) 140 may be connected to and/or communicate with each other via a wireless connection, a wired connection, or a combination thereof.

The ultrasound imaging device 110 refers to a medical device that uses ultrasonic waves to reproduce a structure inside the human body as images. Merely by way of example, the ultrasound imaging device 110 may include a Doppler ultrasound diagnosis device, an ultrasound diagnosis instrument, an ultrasound Doppler flow analyzer, etc. In some embodiments, as shown in FIG. 1, the ultrasound imaging device 110 may include at least one ultrasonic probe 111. The at least one ultrasonic probe 111 may obtain scanning data. Specifically, the at least one ultrasonic probe 111 may emit ultrasonic waves to a target subject or a portion of the target subject and receive reflected ultrasonic waves from the target subject or the portion of the target subject. The reflected ultrasonic waves may be used for generating ultrasound images of the target subject. The ultrasound images may illustrate an internal structure of the target subject. It should be noted that the ultrasound imaging device 110 described herein is merely provided for illustration purposes, and not intended to limit the scope of the present disclosure.

In some embodiments, the target subject may include a human being (e.g., a patient), an animal, or a specific portion, organ, and/or tissue thereof. Merely by way of example, the target subject may include head, chest, abdomen, heart, liver, upper limbs, lower limbs, or the like, or any combination thereof. In the present disclosure, the term "object" or "subject" are used interchangeably in the present disclosure.

In some embodiments, the processing device 120 may be a single server or a server group. The server group may be centralized or distributed. The processing device 120 may process data and/or information obtained from the ultrasound imaging device 110, the storage device 130, and/or the user terminal(s) 140. For example, the processing device 120 may determine a target clinical scene associated with the target subject and determine at least one ultrasound probe corresponding to the target clinical scene based on a corresponding relationship between clinical scenes and ultrasound probes. Further, the processing device 120 may determine a target ultrasound probe from the at least one ultrasound probe and generate an ultrasound image of the target subject by causing the ultrasound imaging device 110 to perform the ultrasound imaging using the target ultrasound probe. In some embodiments, the processing device 120 may be local or remote from the ultrasound imaging system 100. In some embodiments, the processing device 120 may be implemented on a cloud platform. In some embodiments, the processing device 120 or a portion of the processing device 120 may be integrated into the ultrasound imaging device 110 and/or the user terminal(s) 140. It should be noted that the processing device 120 in the present disclosure may include one or multiple processors. Thus operations and/or method steps that are performed by one processor may also be jointly or separately performed by the multiple processors.

The storage device 130 may store data, instructions, and/or any other information. In some embodiments, the storage device 130 may store data obtained from the ultrasound imaging device 110, the processing device 120, and/or the user terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. In some embodiments, the storage device 130 may be implemented on a cloud platform. In some embodiments, the storage device 130 may be part of the ultrasound imaging device 110, the processing device 120, and/or the user terminal(s) 140.

The user terminal(s) 140 may be configured to enable a user interaction between a user and the ultrasound imaging system 100. In some embodiments, the user terminal(s) 140 may be connected to and/or communicate with the ultrasound imaging device 110, the processing device 120, and/or the storage device 130. In some embodiments, the user terminal(s) 140 may include a mobile device 141, a tablet computer 142, a laptop computer 143, or the like, or a combination thereof. In some embodiments, the user terminal(s) 140 may be part of the processing device 120 and/or the ultrasound imaging device 110.

The network 150 may include any suitable network that can facilitate the exchange of information and/or data for the ultrasound imaging system 100. In some embodiments, one or more components of the ultrasound imaging system 100 (e.g., the ultrasound imaging device 110, the processing device 120, the storage device 130, the user terminal(s) 140, etc.) may communicate information and/or data with one or more other components of the ultrasound imaging system 100 via the network 150.

It should be noted that the above description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the ultrasound imaging system 100 may include one or more additional components and/or one or more components described above may be omitted. Additionally or alternatively, two or more components of the ultrasound imaging system 100 may be integrated into a single component. For example, the processing device 120 may be integrated into the ultrasound imaging device 110. As another example, a component of the ultrasound imaging system 100 may be replaced by another component that can implement the functions of the component. However, those variations and modifications do not depart from the scope of the present disclosure.

Figure 2:
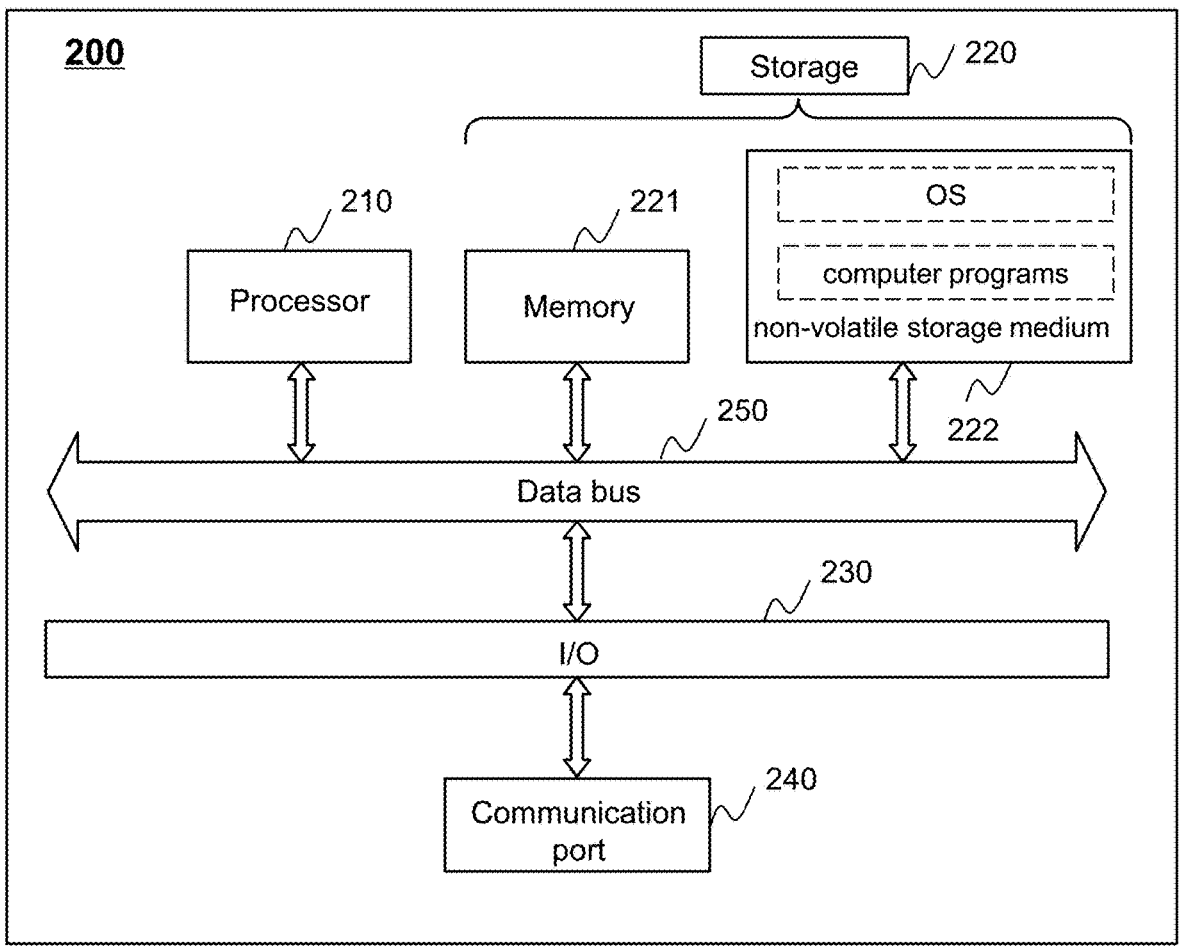
FIG. 2 is a schematic diagram illustrating exemplary hardware and/or software components of a computing device according to some embodiments of the present disclosure.

FIG. 2 is a schematic diagram illustrating exemplary hardware and/or software components of a computing device 200 according to some embodiments of the present disclosure. The computing device 200 may be used to implement any component of the ultrasound imaging system 100 as described herein. For example, the processing device 120 and/or a user terminal 140 may be implemented on the computing device 200, respectively, via its hardware, software program, firmware, or a combination thereof. Although only one such computing device is shown, for convenience, the computer functions relating to the ultrasound imaging system 100 as described herein may be implemented in a distributed fashion on a number of similar platforms, to distribute the processing load. As illustrated in FIG. 2, the computing device 200 may include a processor 210, a storage 220, an input/output (I/O) 230, a communication port 240, and a data bus 250.

The processor 210 may execute computer instructions (e.g., program code) and perform functions of the processing device 120 in accordance with techniques described herein. The storage 220 may store data/information obtained from the ultrasound imaging device 110, the storage device 130, the user terminal(s) 140, and/or any other component of the ultrasound imaging system 100. In some embodiments, the storage 220 may store one or more programs and/or instructions to perform exemplary methods described in the present disclosure. In some embodiments, the storage 220 may include a memory 221 and a non-volatile storage medium 222. In some embodiments, the non-volatile storage medium 222 may store an operating system (OS) (e.g., iOS™, Android™, Windows Phone™, etc.), computer programs. The I/O 230 may input and/or output signals, data, information, etc. In some embodiments, the I/O 230 may enable a user interaction with the processing device 120. In some embodiments, the I/O 230 may include an input device by which the user may input the signals, data, and/or information. In some embodiments, the I/O 230 may include a display interface by which the computing device 200 may output the signals, data, and/or information. The communication port 240 may be connected to a network (e.g., the network 150) to facilitate data communications. The data bus 250 may be configured to implement data communications among components of the computing device 200.

Figure 3:
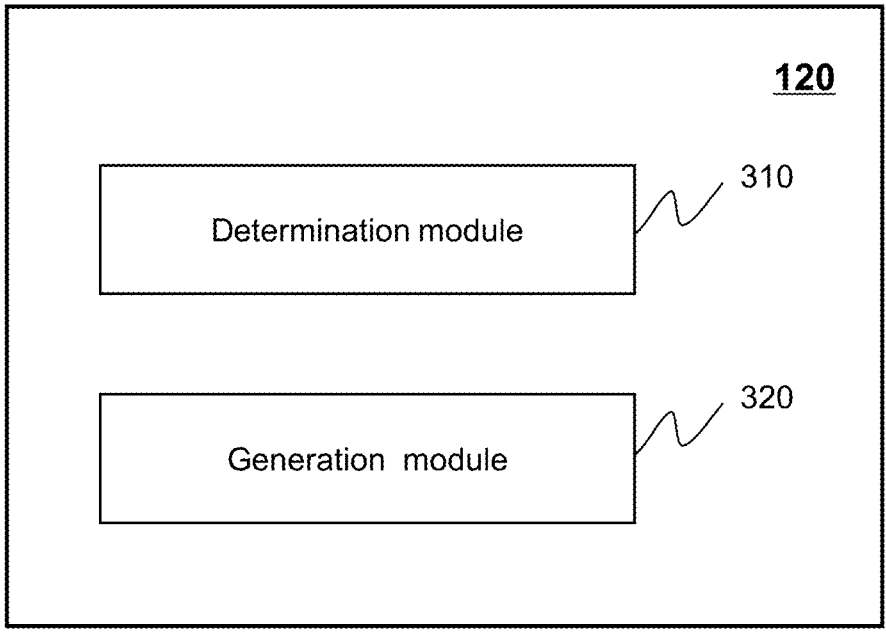
FIG. 3 is a block diagram illustrating an exemplary processing device according to some embodiments of the present disclosure.

FIG. 3 is a block diagram illustrating an exemplary processing device 120 according to some embodiments of the present disclosure. As shown in FIG. 3, the processing device 120 may include a determination module 310 and a generation module 320.

The determination module 310 may be configured to determine a target clinical scene associated with a target subject. More descriptions of the determining the target clinical scene may be found elsewhere in the present disclosure (e.g., operations 410 and the descriptions thereof).

The determination module 310 may be configured to determine at least one ultrasound probe corresponding to the target clinical scene based on a corresponding relationship between clinical scenes and ultrasound probes. More descriptions of the determining the at least one ultrasound probe may be found elsewhere in the present disclosure (e.g., operations 420 and the descriptions thereof).

The determination module 310 may be further configured to determine a target ultrasound probe from the at least one ultrasound probe. More descriptions of the determining the target ultrasound probe may be found elsewhere in the present disclosure (e.g., operations 430 and the descriptions thereof).

The generation module 320 may be configured to generate an ultrasound image of the target subject by performing the ultrasound imaging using the target ultrasound probe. More descriptions of the generating the ultrasound image may be found elsewhere in the present disclosure (e.g., operations 440 and the descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may include one or more additional modules, such as a storage module (not shown) for storing data.

FIG. 4 is a flowchart illustrating an exemplary ultrasound imaging process 400 according to some embodiments of the present disclosure. In some embodiments, process 400 may be executed by the ultrasound imaging system 100. For example, the process 400 may be implemented as a set of instructions (e.g., an application) stored in a storage device (e.g., the storage device 130), and the processing device 120 (e.g., one or more modules illustrated in FIG. 3) may execute the set of instructions and may accordingly be directed to perform the process 400.

In 410, the processing device 120 (e.g., the determination module 310) may determine a target clinical scene associated with a target subject.

The target clinical scene may be related to an examination need of the target subject. In some embodiments, the examination need of the target subject may relate to one or more examination parts of the target subject that need to be examined, an examination item that the target subject needs to receive, and/or a disease category of the target subject. Merely by way of example, the one or more examination parts of the target subject may include head, chest, breast, abdomen, heart, liver, upper limbs, lower limbs, or the like, or any combination thereof. Merely by way of example, the examination item of the target subject may include a gynecological examination, a physical examination, a prenatal examination, or the like, or any combination thereof. Merely by way of example, the disease category of the target subject may include mild illness, severe illness, emergency illness, emergency and severe illness, or the like.

In some embodiments, the examination need of the target subject may be related to a physical characteristic (e.g., age, body shape, gender) of the target subject. Merely by way of example, the physical characteristic of the target subject may include age, body shape, gender, or the like, or any combination thereof. For example, target subjects of different ages have different examination needs, and accordingly, clinical scenes (or scenarios) associated with the target subjects are different.

In some embodiments, the processing device 120 may obtain first feature information of the target subject and determine the target clinical scene based on the first feature information. The first feature information may be related to the examination need and/or physical characteristics of the target subject. For example, multiple preset clinical scenes may be previously defined, and different preset clinical scenes may correspond to subjects with different first feature information. The processing device 120 may select the target clinical scene from the multiple preset clinical scenes based on the first feature information of the target subject.

In the embodiments of the present disclosure, the target clinical scene is determined based on the first feature information related to the examination need and/or physical characteristics of the target subject, so that a target ultrasound probe subsequently determined based on the target clinical scene is consistent with the needs of the target object, thereby improving the efficiency and accuracy of ultrasound imaging.

In some embodiments, the processing device 120 may obtain second feature information of an operator (e.g., a doctor) of the ultrasound imaging and determine the target clinical scene based on the first feature information and the second feature information. The second feature information may be related to the department and/or the preference of the operator. The department of the operator may reflect the medical field in which the operator specializes, and the preference of the operator may reflect the operating habits of the operator. For example, in the multiple preset clinical scenes, different preset clinical scenes may correspond to subjects with different first feature information and operators with different second feature information. The processing device 120 may select the target clinical scene from the multiple preset clinical scenes based on the first feature information of the target subject and the second feature information of the operator.

In the embodiments of the present disclosure, the target clinical scene is determined based on the first feature information related to the examination need and/or physical characteristics of the target subject and the second feature information related to the department and/or the preference of the operator, so that the target ultrasound probe subsequently determined based on the target clinical scene is consistent with the needs of the target object and the operator, thereby improving the efficiency and accuracy of ultrasound imaging.

In some embodiments, the processing device 120 may display the multiple preset clinical scenes via a user terminal (e.g., the user terminal 140) communicatively connected to the processing device 120. The operator may select, via the user terminal, one preset clinical scene from the multiple preset clinical scenes as needed. When one preset clinical scene is selected, the user terminal may send a first trigger instruction for selecting the preset clinical scene from the multiple preset clinical scenes to the processing device 120. The processing device 120 may receive the first trigger instruction via the user terminal and designate the selected preset clinical scene as the target clinical scene.

In the embodiments of the present disclosure, the target clinical scene is selected manually by the operator, which broadens the way for determining the target clinical scene, thereby expanding the scope of application of ultrasound imaging systems.

In some embodiments, the multiple preset clinical scenes may be displayed on the user terminal. For example, the user terminal may include a display interface configured to display the multiple preset clinical scenes. More descriptions of the display of the multiple preset clinical scenes may be found elsewhere in the present disclosure (e.g., FIGS. 5-6 and the descriptions thereof).

In 420, the processing device 120 (e.g., the determination module 310) may determine at least one ultrasound probe corresponding to the target clinical scene based on a corresponding relationship between clinical scenes and ultrasound probes.

Figure 8:
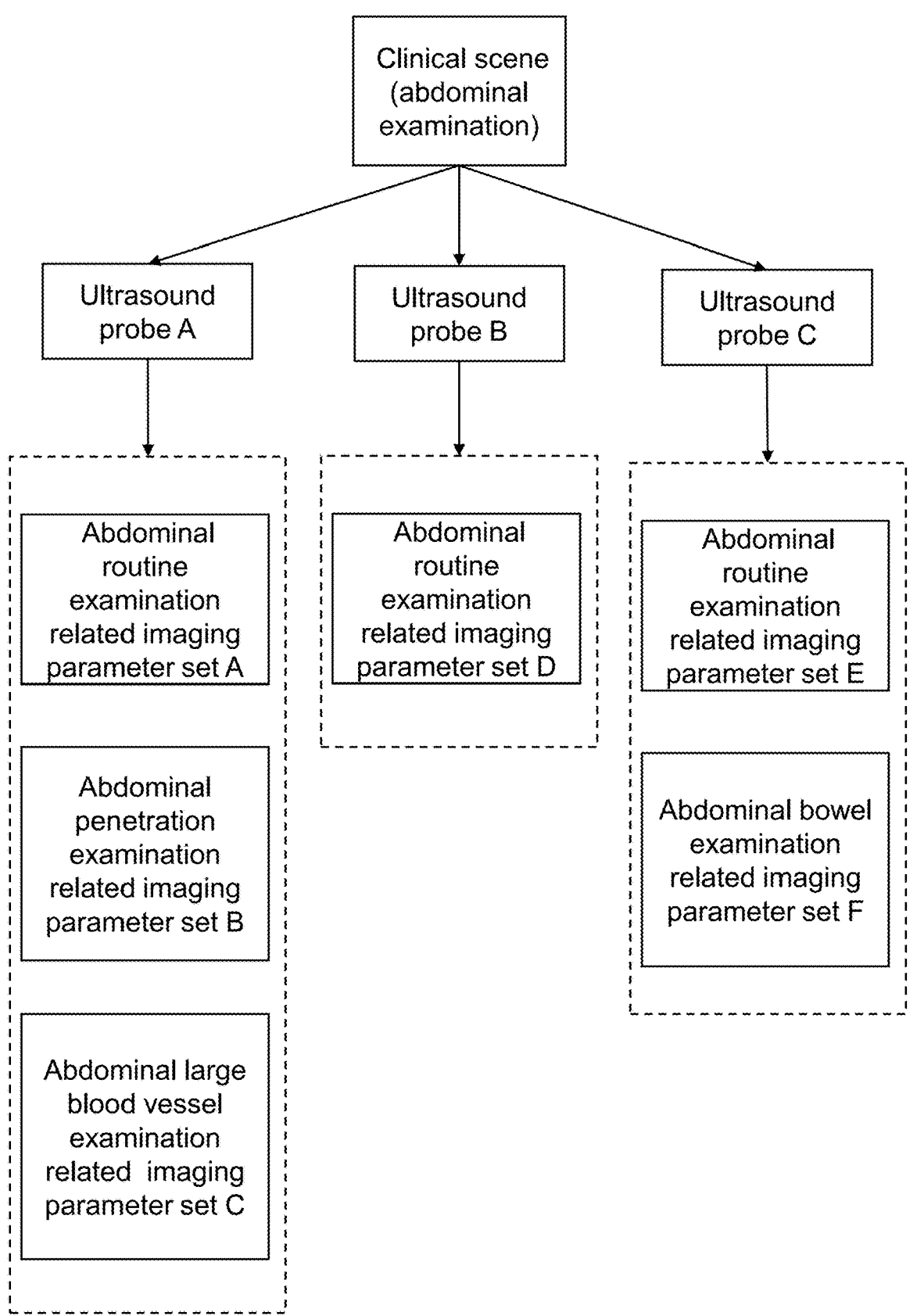
FIG. 8 is a schematic diagram illustrating an exemplary corresponding relationship between clinical scenes and ultrasound probes and an exemplary corresponding relationship between ultrasound probes and imaging parameter sets according to some embodiments of the present disclosure.

In some embodiments, the corresponding relationship between clinical scenes and ultrasound probes may be preset. A clinical scene may correspond to at least one ultrasound probe. Merely by way of example, the at least one ultrasound probe may include a convex array probe, a linear array probe, a phased array probe, a high frequency linear array probe, a cavity probe, a three-dimensional probe, a four-dimensional volume probe, or the like, or any combination thereof. For illustration purposes, FIG. 8 illustrates an exemplary corresponding relationship between a clinical scene and ultrasound probes according to some embodiments of the present disclosure. As shown in FIG. 8, a clinical scene related to an abdominal examination of the target subject may correspond to an ultrasound probe A, an ultrasound probe B, and an ultrasound probe C.

In 430, the processing device 120 (e.g., the determination module 310) may determine a target ultrasound probe from the at least one ultrasound probe.

In some embodiments, when the at least one ultrasound probe corresponding to the target clinical scene includes one ultrasound probe, the processing device 120 may designate the ultrasound probe as the target ultrasound probe. In some embodiments, when the at least one ultrasound probe corresponding to the target clinical scene includes multiple ultrasound probes, the processing device 120 may actuate one ultrasound probe among the multiple ultrasound probes and designate the actuated ultrasound probe as the target ultrasound probe.

In some embodiments, the actuated ultrasound probe may be selected based on a ranking result of the multiple ultrasound probes, and the ranking result of the multiple ultrasound probes is determined based on at least one of a usage frequency of each of the multiple ultrasound probes, a last usage time of each of the multiple ultrasound probes, or a fault record of each of the multiple ultrasound probes. For example, the ultrasonic probe with higher usage frequency has higher ranking; the ultrasonic probe whose last usage time is closer to the current time has higher ranking; or the ultrasonic probe with fewer faults has higher ranking. The processing device 120 may designate the ultrasound probe with the highest ranking among the multiple ultrasound probes as the actuated ultrasound probe.

In the embodiments of the present disclosure, the determination of the actuated ultrasound probe is performed based on the usage frequency, the last usage time, or the fault record of each of the multiple ultrasound probes, which makes the determined target ultrasound probe better satisfy actual needs, thereby improving the efficiency and accuracy of ultrasound imaging.

In some embodiments, the actuated ultrasound probe may be selected from the multiple ultrasound probes based on the first feature information of the target subject and/or the second feature information of the operator using a first machine learning model (e.g., a neural network model). For example, the processing device 120 may select the actuated ultrasound probe from the multiple ultrasound probes by inputting types or operating parameters of the multiple ultrasound probes and the first feature information of the target subject and/or the second feature information of the operator into the first machine learning model. In some embodiments, the first machine learning model is pre-trained and stored in a storage device (e.g., the storage device 130) disclosed elsewhere in the present disclosure or a database of a vendor or manufacturer that provides and/or updates the first machine learning model. The processing device 120 may retrieve the first machine learning model from the storage device or the database.

In the embodiments of the present disclosure, the actuated ultrasound probe is selected based on the first feature information of the target subject and/or the second feature information of the operator using the first machine learning model, which improves the efficiency of selecting the actuated ultrasound probe, and makes the determined target ultrasound probe be consistent with the needs of the target object and/or the operator, thereby improving the efficiency and accuracy of ultrasound imaging.

In some embodiments, the processing device 120 may display the actuated ultrasound probe via the user terminal (e.g., the user terminal 140) communicatively connected to the processing device 120. The operator may modify the actuated ultrasound probe by clicking on the actuated ultrasound probe. For example, when the operator clicks on the actuated ultrasound probe, the user terminal may display other ultrasound probes among the multiple ultrasound probes. The operator may replace the actuated ultrasound probe with another ultrasound probe among the other ultrasound probes.

In some embodiments, the processing device 120 may display the multiple ultrasound probes via the user terminal (e.g., the user terminal 140) communicatively connected to the processing device 120. The operator may select, via the user terminal, one ultrasound probe from the multiple ultrasound probes as needed. When one ultrasound probe is selected, the user terminal may send a second trigger instruction for selecting the ultrasound probe from the multiple ultrasound probes to the processing device 120. The processing device 120 may receive the second trigger instruction via the user terminal and designate the selected ultrasound probe as the target ultrasound probe.

In the embodiments of the present disclosure, the target ultrasound probe is selected manually by the operator, which broadens the way for determining the target ultrasound probe, thereby expanding the scope of application of ultrasound imaging systems.

In some embodiments, the multiple ultrasound probes may be displayed on the user terminal e.g., via a list of the multiple ultrasound probes. The operator may perform an activation operation (e.g., clicking on a preset button) on the user terminal, so that the multiple ultrasound probes are in an updateable state. The operator may delete or modify any one of the multiple ultrasound probes in the updateable state displayed on the user terminal, or add a new ultrasound probe into the multiple ultrasound probes displayed on the user terminal.

In 440, the processing device 120 (e.g., the determination module 310) may generate an ultrasound image of the target subject by performing the ultrasound imaging using the target ultrasound probe.

In some embodiments, the processing device 120 may determine at least one preset imaging parameter set corresponding to the target ultrasound probe based on a corresponding relationship between ultrasound probes and imaging parameter sets. Further, the processing device 120 may determine a target imaging parameter set from the at least one preset imaging parameter set and perform the ultrasound imaging based on the target imaging parameter set using the target ultrasound probe. More descriptions of the determination of the target imaging parameter set may be found elsewhere in the present disclosure (e.g., FIG. 7 and the descriptions thereof).

In some embodiments, the processing device 120 may determine a target image processing parameter set corresponding to the target clinical scene based on a corresponding relationship between clinical scenes and image processing parameter sets. Further, the processing device 120 may process the ultrasound image based on the target image processing parameter set. More descriptions of the processing of the ultrasound image may be found elsewhere in the present disclosure (e.g., FIG. 9 and the descriptions thereof).

In some embodiments, the processing device 120 may determine a target position parameter, corresponding to the target clinical scene, of an ultrasound imaging device (e.g., the ultrasound imaging device 110) configured to perform the ultrasound imaging based on a corresponding relationship between clinical scenes and multiple position parameters of the ultrasound imaging device. Merely by way of example, a position parameter includes a position and an angle of the ultrasound imaging device relative to a subject, a position and an angle of the ultrasound probe of the ultrasound imaging device. Further, before performing the ultrasound imaging, the ultrasound imaging device may be moved based on the target position parameter of the ultrasound imaging device. For example, before performing the ultrasound imaging, the position and the angle of the ultrasound imaging device relative to the target subject may be adjusted based on the target position parameter.

According to the embodiments of the present disclosure, after the target clinical scene is determined, the target ultrasound probe, the target imaging parameter set, and/or the target image processing parameter set can be automatically determined based on the target clinical scene, which eliminates the need for the operator to manually set the ultrasound probe, the corresponding imaging parameter set, the corresponding image processing parameter set, thereby simplifying the display interface, operating buttons, and/or operating functions of the ultrasound imaging device, and accordingly, improving the convenience, standardization, and efficiency of the ultrasound imaging. In addition, the imaging process is user-friendly and can be easily performed by the operators (including inexperienced operators), thereby making the ultrasound imaging systems and methods provided in the embodiments of the present disclosure highly practical.

Figure 5:
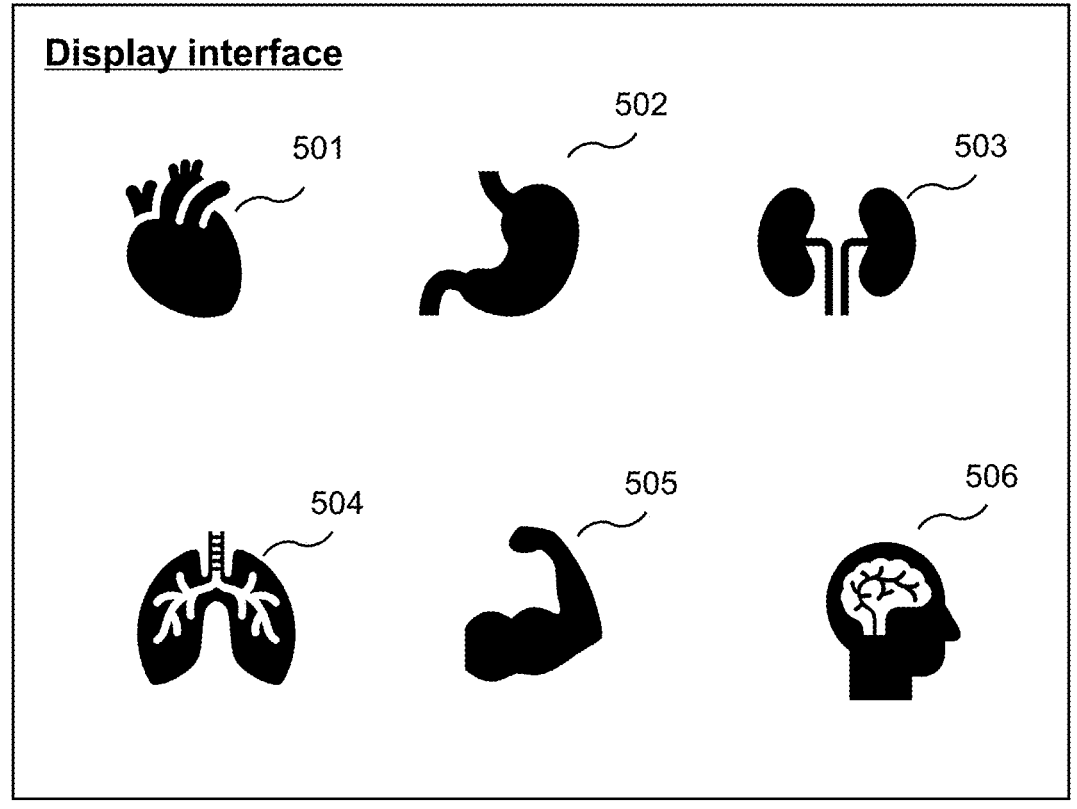
FIG. 5 is a schematic diagram illustrating exemplary visual elements representing multiple preset clinical scenes according to some embodiments of the present disclosure.

FIG. 5 is a schematic diagram illustrating exemplary visual elements representing multiple preset clinical scenes according to some embodiments of the present disclosure.

As described in connection with FIG. 4, the multiple preset clinical scenes may be displayed on the user terminal, for example, a display interface of the user terminal. As shown in FIG. 5, the visual elements representing the multiple preset clinical scenes are displayed on the display interface of the user terminal. In some embodiments, each of the visual elements includes an icon representing a scanning part of the corresponding preset clinical scene. For example, as shown in FIG. 5, a visual element 501 representing cardiac-related preset clinical scene includes an icon representing the heart, a visual element 502 representing a gastric-related preset clinical scene includes an icon representing the stomach, a visual element 503 representing a renal-related preset clinical scene includes an icon representing the kidneys, a visual element 504 representing a pulmonary-related preset clinical scene includes an icon representing the lungs, a visual element 505 representing an upper limb-related preset clinical scene includes an icon representing the upper limb, and a visual element 506 representing a brain-related preset clinical scene includes an icon representing the brain.

In some embodiments, a display manner of the visual elements on the user terminal (e.g., the display interface) may be determined based on the second feature information of the operator of the ultrasound imaging. For example, when the operator logs into the processing device 120, the processing device 120 may obtain the second feature information of the operator based on an identity used by the operator to log into the processing device 120, and cause the user terminal to display the visual elements based on the feature information of the operator.

In some embodiments, an arrangement of the visual elements on the user terminal may be determined based on the second feature information of the operator of the ultrasound imaging. For example, as shown in FIG. 5, when the department of the operator is cardiology, the processing device 120 may cause the user terminal to rank the visual element 501 representing cardiac-related preset clinical scene ahead of the visual elements (e.g., 502, 503, 504, 505, and 506) representing other preset clinical scenes. As another example, the processing device 120 may cause the user terminal to rank visual elements representing the operator's preferred preset clinical scenes at a more ahead position than visual elements representing other preset clinical scenes.

In some embodiments, the visual elements on the user terminal may be enlarged based on the second feature information of the operator of the ultrasound imaging. For example, when the department of the operator is cardiology, the processing device 120 may cause the user terminal to enlarge the visual element 501 representing a cardiac-related preset clinical scene. As another example, the processing device 120 may cause the user terminal to enlarge the visual elements representing the operator's preferred preset clinical scenes.

In some embodiments, the display manner of the visual elements on the user terminal may be manually adjusted by the operator. For example, the arrangement of the visual elements on the user terminal may be manually adjusted by the operator. Merely by way of example, the operator may drag any one visual element to place it where he/she wants. As another example, whether the visual elements on the user terminal are enlarged or not may be manually adjusted by the operator. Merely by way of example, the operator may enlarge any one visual element by clicking it.

In some embodiments, the operator may select a preset clinical scene by clicking the visual element representing the preset clinical scene. Further, the processing device 120 may designate the selected preset clinical scene as the target clinical scene.

In the embodiments of the present disclosure, the display manner of the visual elements on the user terminal is determined based on the second feature information of the operator or is manually adjusted by the operator, which makes it easier for the operator to find the clinical scene he/her may need, thereby improving the efficiency of the ultrasound imaging.

Figure 6:
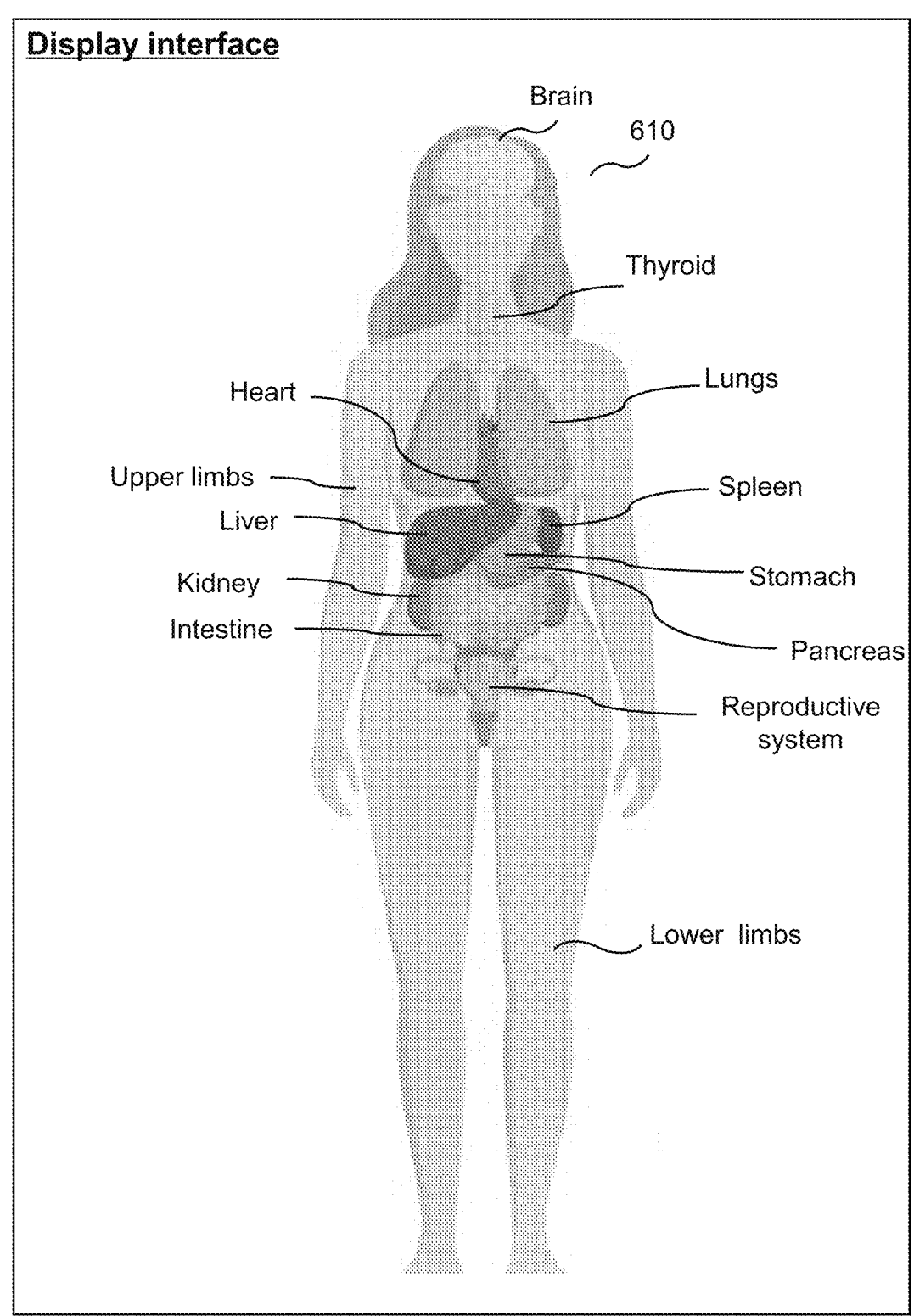
FIG. 6 is a schematic diagram illustrating an exemplary body model representing a target subject according to some embodiments of the present disclosure.

FIG. 6 is a schematic diagram illustrating an exemplary body model representing a target subject according to some embodiments of the present disclosure. The body model may include multiple scanning parts representing the multiple preset clinical scenes. For example, as shown in FIG. 6, a body model 610 may include scanning parts such as brain, thyroid, lungs, heart, liver, spleen, stomach, pancreas, kidneys, intestine, reproductive system, upper limbs, lower limbs, etc. In some embodiments, the operator may select a preset clinical scene by clicking the scanning part corresponding to the preset clinical scene. Further, the processing device 120 may designate the selected preset clinical scene as the target clinical scene.

In some embodiments, the body model representing the target subject and the visual elements representing the multiple preset clinical scenes may be both displayed on the display interface of the user terminal.

In the embodiments of the present disclosure, the multiple preset clinical scenes are displayed on the display interface of the user terminal in the form of a more vivid human body model, which facilitates the operator to select the desired clinical scene, thereby improving the efficiency of ultrasound imaging.

FIG. 7 is a flowchart illustrating an exemplary ultrasound imaging process according to some embodiments of the present disclosure. In some embodiments, the process 700 may be performed to achieve at least part of operation 440 as described in connection with FIG. 4.

In 710, the processing device 120 (e.g., the generation module 320) may determine at least one preset imaging parameter set corresponding to the target ultrasound probe based on a corresponding relationship between ultrasound probes and imaging parameter sets.

In some embodiments, a preset imaging parameter set refers to a set of parameters used by the ultrasound imaging system in the process of performing the ultrasound imaging on a subject.

In some embodiments, the corresponding relationship between ultrasound probes and imaging parameter sets may be preset. An ultrasound probe may correspond to at least one imaging parameter set. For illustration purposes, FIG. 8 illustrates an exemplary corresponding relationship between ultrasound probes and imaging parameter sets according to some embodiments of the present disclosure. As shown in FIG. 8, an ultrasound probe A corresponds to three imaging parameter sets including an abdominal routine examination related imaging parameter set A, an abdominal penetration examination related imaging parameter set B, and an abdominal large blood vessel examination related imaging parameter set C; an ultrasound probe B corresponds to one imaging parameter set including an abdominal routine examination related imaging parameter set D; and an ultrasound probe C corresponds to two imaging parameter sets including an abdominal routine examination related imaging parameter set E and an abdominal bowel examination related imaging parameter set F.

In 720, the processing device 120 (e.g., the generation module 320) may determine a target imaging parameter set from the at least one preset imaging parameter set.

In some embodiments, when the at least one preset imaging parameter set corresponding to the target ultrasound probe includes one preset imaging parameter set, the processing device 120 may designate the preset imaging parameter set as the target preset imaging parameter set. In some embodiments, when the at least one preset imaging parameter set corresponding to the target ultrasound probe includes multiple preset imaging parameter sets, the processing device 120 may actuate one preset imaging parameter set among the multiple preset imaging parameter sets and designate the actuated preset imaging parameter set as the target preset imaging parameter set.

In some embodiments, the actuated preset imaging parameter set may be selected based on a ranking result of the multiple preset imaging parameter sets, and the ranking result of the multiple preset imaging parameter sets is determined based on at least one of a usage frequency of each of the multiple preset imaging parameter sets, a last usage time of each of the multiple preset imaging parameter sets, or a fault record associated with a usage of each of the multiple preset imaging parameter sets. For example, the preset imaging parameter set with higher usage frequency has a higher ranking; the preset imaging parameter set whose last usage time is closer to the current time has a higher ranking; or when the preset imaging parameter set is used, the fewer the number of the ultrasound imaging faults that occur, the preset imaging parameter set has a higher ranking. The processing device 120 may designate the preset imaging parameter set with the highest ranking among the multiple preset imaging parameter sets as the actuated preset imaging parameter set.

In the embodiments of the present disclosure, the determination of the actuated preset imaging parameter set is performed based on the usage frequency or the last usage time of each of the multiple preset imaging parameter sets, or the fault record associated with the usage of each of the multiple preset imaging parameter sets, which makes the determined target preset imaging parameter set better satisfy actual needs, thereby improving the efficiency and accuracy of ultrasound imaging.

In some embodiments, the actuated preset imaging parameter set may be selected from the multiple preset imaging parameter sets based on the first feature information of the target subject and/or the second feature information of the operator using a second machine learning model (e.g., a neural network model). For example, the processing device 120 may select the actuated preset imaging parameter set from the multiple preset imaging parameter sets by inputting types of the multiple preset imaging parameter sets or the multiple preset imaging parameter sets and the first feature information of the target subject and/or the second feature information of the operator into the second machine learning model. In some embodiments, the second machine learning model is pre-trained and stored in a storage device (e.g., the storage device 130) disclosed elsewhere in the present disclosure or a database of a vendor or manufacturer that provides and/or updates the second machine learning model. The processing device 120 may retrieve the second machine learning model from the storage device or the database.

In the embodiments of the present disclosure, the actuated preset imaging parameter set is selected based on the first feature information of the target subject and/or the second feature information of the operator using the second machine learning model, which improves the efficiency of selecting the actuated preset imaging parameter set, and makes determined target preset imaging parameter set be consistent with the needs of the target object and/or the operator, thereby improving the efficiency and accuracy of ultrasound imaging.

In some embodiments, the processing device 120 may display the actuated preset imaging parameter set via the user terminal (e.g., the user terminal 140) communicatively connected to the processing device 120. The operator may modify the actuated preset imaging parameter set by clicking on the actuated preset imaging parameter set. For example, when the operator clicks on the actuated preset imaging parameter set, the user terminal may display other preset imaging parameter sets among the multiple preset imaging parameter sets. The operator may replace the actuated preset imaging parameter set with another preset imaging parameter set among the other preset imaging parameter sets.

In some embodiments, the processing device 120 may display the multiple preset imaging parameter sets via a user terminal (e.g., the user terminal 140) communicatively connected to the processing device 120. The operator may select, via the user terminal, one preset imaging parameter set from the multiple preset imaging parameter sets as needed. When one preset imaging parameter set is selected, the user terminal may send a third trigger instruction for selecting the preset imaging parameter set from the multiple preset imaging parameter sets to the processing device 120. The processing device 120 may receive the third trigger instruction via the user terminal and designate the selected preset imaging parameter set as the target preset imaging parameter set.

In the embodiments of the present disclosure, the target preset imaging parameter set is selected manually by the operator, which broadens the way for determining the target preset imaging parameter set, thereby expanding the scope of application of ultrasound imaging systems.

In some embodiments, the multiple preset imaging parameter sets may be displayed on the user terminal e.g., via a list of the multiple preset imaging parameter sets. The operator may perform an activation operation (e.g., clicking on a preset button) on the user terminal, so that the multiple preset imaging parameter sets are in an updateable state. The operator may delete or modify any one of the preset imaging parameter sets in the updateable state displayed on the user terminal, or add a new preset imaging parameter set into the multiple preset imaging parameter sets displayed on the user terminal.

In 430, the processing device 120 (e.g., the generation module 320) may perform the ultrasound imaging based on the target imaging parameter set using the target ultrasound probe.

FIG. 9 is a flowchart illustrating an exemplary ultrasound imaging process 900 according to some embodiments of the present disclosure. In some embodiments, process 900 may be executed by the ultrasound imaging system 100. For example, the process 900 may be implemented as a set of instructions (e.g., an application) stored in a storage device (e.g., the storage device 130), and the processing device 120 (e.g., one or more modules illustrated in FIG. 3) may execute the set of instructions and may accordingly be directed to perform the process 900.

In 910, the processing device 120 (e.g., the determination module 310) may determine a target clinical scene associated with a target subject.

In 920, the processing device 120 (e.g., the determination module 310) may determine at least one ultrasound probe corresponding to the target clinical scene based on a corresponding relationship between clinical scenes and ultrasound probes.

In 930, the processing device 120 (e.g., the determination module 310) may determine a target ultrasound probe from the at least one ultrasound probe.

Operations 910-930 may be performed in a similar manner to operations 410-430 as described in connection with FIG. 4, respectively.

In 940, the processing device 120 (e.g., the generation module 320) may determine at least one preset imaging parameter set corresponding to the target ultrasound probe based on a corresponding relationship between ultrasound probes and imaging parameter sets.

In 950, the processing device 120 (e.g., the generation module 320) may determine a target imaging parameter set from the at least one preset imaging parameter set.

In 960, the processing device 120 (e.g., the generation module 320) may generate an ultrasound image of the target subject by performing the ultrasound imaging based on the target imaging parameter set using the target ultrasound probe.

Operations 940-960 may be performed in a similar manner to operations 710-730 as described in connection with FIG. 7, respectively.

In 970, the processing device 120 (e.g., the generation module 320) may determine a target image processing parameter set corresponding to the target clinical scene based on a corresponding relationship between clinical scenes and image processing parameter sets.

In some embodiments, an image processing parameter set refers to a set of parameters used by the ultrasound imaging system in the process of processing an ultrasound image. In some embodiments, the image processing parameter set may include a measurement package, an annotation library, and/or a report template. The measurement package may include quantitative parameter(s) that need to be determined by processing an ultrasound image. For example, when the clinical scene is a heart-related clinical scene, the quantitative parameter(s) may include a size of the atrium and/or ventricle, etc. As another example, the clinical scene is a prenatal-related clinical scene, the quantitative parameter(s) may include fetal biparietal diameter, head circumference, etc. The annotation library may include preset annotation(s) that need to be added to an ultrasound image.

In some embodiments, the corresponding relationship between clinical scenes and image processing parameter sets may be preset. A clinical scene may correspond to one image processing parameter set.

In 980, the processing device 120 (e.g., the generation module 320) may process the ultrasound image based on the target image processing parameter set.

In some embodiments, the processing device 120 may perform a measurement operation on the ultrasound image based on the measurement package to obtain measurement data corresponding to the quantitative parameter(s) in the measurement package.

In some embodiments, the processing device 120 may annotate the ultrasound image based on the annotation library. For example, the processing device 120 may add the preset annotations in the annotation library on the ultrasound image.

In some embodiments, the processing device 120 may generate a report of the ultrasound imaging based on the report template. For example, the processing device 120 may generate the report of the ultrasound imaging by writing the measurement data and the annotated ultrasound image into the report template. In some embodiments, the processing device 120 may display the report via a user terminal (e.g., the user terminal 140) communicatively connected to the processing device 120. The operator may modify the report via the user terminal.

The operations of the illustrated processes 400, 700, and 900 presented above are intended to be illustrative. In some embodiments, a process may be accomplished with one or more additional operations not described, and/or without one or more of the operations discussed. Additionally, the order in which the operations of a process described above is not intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" may mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (Saas).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/ or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for ultrasound imaging, implemented on a computing device including at least one processor and at least one storage device, the method comprising:

determining a target clinical scene associated with a target subject;

determining, automatically by the computing device and based on a first corresponding relationship between clinical scenes and ultrasound probes, at least one ultrasound probe corresponding to the target clinical scene;

determining, automatically by the computing device, a target ultrasound probe from the at least one ultrasound probe;

determining, automatically by the computing device, at least one preset imaging parameter set corresponding to the target ultrasound probe based on a second corresponding relationship between ultrasound probes and imaging parameter sets;

determining, automatically by the computing device, a target imaging parameter set from the at least one preset imaging parameter set;

generating, automatically by the computing device, an ultrasound image of the target subject by performing the ultrasound imaging based on the target imaging parameter set using the target ultrasound probe;

determining, automatically by the computing device, a target image processing parameter set corresponding to the target clinical scene based on a third corresponding relationship between the clinical scenes and image processing parameter sets, wherein each of the image processing parameter sets is a set of parameters used in a process of processing the ultrasound image; and processing, automatically by the computing device, the ultrasound image based on the target image processing parameter set.

2. The method of claim 1, wherein determining the target clinical scene associated with the target subject includes determining, automatically by the computing device, the target clinical scene associated with the target subject by:

obtaining, automatically by the computing device, first feature information of the target subject, the first feature information being related to the examination need and/or physical characteristics of the target subject; and determining, automatically by the computing device, the target clinical scene based on the first feature information.

3. The method of claim 2, wherein determining, automatically by the computing device, the target clinical scene based on the first feature information includes:

obtaining, automatically by the computing device, second feature information of an operator of the ultrasound imaging, the second feature information being related to the department and/or the preference of the operator; and determining, automatically by the computing device, the target clinical scene based on the first feature information and the second feature information.

4. The method of claim 1, wherein determining the target clinical scene associated with the target subject includes:

displaying multiple preset clinical scenes via a user terminal communicatively connected to the computing device;

receiving, via the user terminal, a first trigger instruction for selecting one preset clinical scene from the multiple preset clinical scenes; and designating the selected preset clinical scene as the target clinical scene.

5. The method of claim 4, wherein visual elements representing the multiple preset clinical scenes are displayed on the user terminal, and an arrangement of the visual elements on the user terminal is determined based on second feature information of an operator of the ultrasound imaging.

6. The method of claim 4, wherein visual elements representing the multiple preset clinical scenes are displayed on the user terminal, and each of the visual elements includes an icon representing a scanning part of the corresponding preset clinical scene.

7. The method of claim 4, wherein a body model representing the target subject is displayed on the user terminal, and the body model includes multiple scanning parts representing the multiple preset clinical scenes.

8. The method of claim 4, wherein visual elements representing the multiple preset clinical scenes are displayed on the user terminal, and the visual elements on the user terminal are enlarged based on second feature information of an operator of the ultrasound imaging.

9. The method of claim 1, wherein when the at least one ultrasound probe corresponding to the target clinical scene includes multiple ultrasound probes, the determining, automatically by the computing device, a target ultrasound probe includes:

actuating one ultrasound probe among the multiple ultrasound probes; and designating the actuated ultrasound probe as the target ultrasound probe.

10. The method of claim 9, wherein the actuated ultrasound probe is selected based on a ranking result of the multiple ultrasound probes, and the ranking result of the multiple ultrasound probes is determined based on at least one of:

a usage frequency of each of the multiple ultrasound probes, a last usage time of each of the multiple ultrasound probes, or a fault record of each of the multiple ultrasound probes.

11. The method of claim 9, wherein the actuated ultrasound probe is selected from the multiple ultrasound probes based on first feature information of the target subject and/or second feature information of an operator using a first machine learning model.

12. The method of claim 1, wherein the each of the image processing parameter sets includes at least one of a measurement package, an annotation library, or a report template.

13. The method of claim 12, wherein the method further includes:

determining a target position parameter, corresponding to the target clinical scene, of an ultrasound imaging device configured to perform the ultrasound imaging based on a corresponding relationship between the clinical scenes and multiple position parameters of the ultrasound imaging device, each of the multiple position parameters includes a position or an angle of the ultrasound imaging device relative to a subject, and a position or an angle of an ultrasound probe of the ultrasound imaging device;

before performing the ultrasound imaging, causing the ultrasound imaging device to move based on the target position parameter of the ultrasound imaging device.

14. The method of claim 1, wherein when the at least one preset imaging parameter set corresponding to the target ultrasound probe includes multiple preset imaging parameter sets, the determining, automatically by the computing device, a target imaging parameter set includes:

actuating one preset imaging parameter set among the multiple preset imaging parameter sets; and designating the actuated preset imaging parameter set as the target imaging parameter set.

15. The method of claim 14, wherein the actuated preset imaging parameter set is selected based on a ranking result of the multiple preset imaging parameter sets, and the ranking result of the multiple preset imaging parameter sets is determined based on at least one of:

a usage frequency of each of the multiple preset imaging parameter sets, a last usage time of each of the multiple preset imaging parameter sets, or a fault record associated with a usage of each of the multiple preset imaging parameter sets.

16. The method of claim 14, wherein the actuated preset imaging parameter set is selected from the multiple preset imaging parameter sets based on first feature information of the target subject and/or second feature information of an operator using a second machine learning model.

17. A system, comprising:

at least one storage device including a set of instructions; and at least one processor in communication with the at least one storage device, wherein when executing the set of instructions, the at least one processor causes the system to perform operations including:

determining a target clinical scene associated with a target subject;

determining, automatically by the at least one processor and based on a first corresponding relationship between clinical scenes and ultrasound probes, at least one ultrasound probe corresponding to the target clinical scene;

determining, automatically by the at least one processor, a target ultrasound probe from the at least one ultrasound probe;

determining, automatically by the at least one processor, at least one preset imaging parameter set corresponding to the target ultrasound probe based on a second corresponding relationship between ultrasound probes and imaging parameter sets;

determining, automatically by the at least one processor, a target imaging parameter set from the at least one preset imaging parameter set;

generating, automatically by the at least one processor, an ultrasound image of the target subject by performing the ultrasound imaging based on the target imaging parameter set using the target ultrasound probe;

determining, automatically by the at least one processor, a target image processing parameter set corresponding to the target clinical scene based on a third corresponding relationship between the clinical scenes and image processing parameter sets, wherein each of the image processing parameter sets is a set of parameters used in a process of processing the ultrasound image; and processing, automatically by the at least one processor, the ultrasound image based on the target image processing parameter set.

18. A non-transitory computer readable medium, comprising executable instructions that, when executed by at least one processor, direct the at least one processor to perform a method, the method comprising:

determining a target clinical scene associated with a target subject;

determining, automatically by the at least one processor and based on a first corresponding relationship between clinical scenes and ultrasound probes, at least one ultrasound probe corresponding to the target clinical scene;

determining, automatically by the at least one processor, a target ultrasound probe from the at least one ultrasound probe;

determining, automatically by the at least one processor, at least one preset imaging parameter set corresponding to the target ultrasound probe based on a second corresponding relationship between ultrasound probes and imaging parameter sets;

determining, automatically by the at least one processor, a target imaging parameter set from the at least one preset imaging parameter set;

generating, automatically by the at least one processor, an ultrasound image of the target subject by performing the ultrasound imaging based on the target imaging parameter set using the target ultrasound probe;

determining, automatically by the at least one processor, a target image processing parameter set corresponding to the target clinical scene based on a third corresponding relationship between the clinical scenes and image processing parameter sets, wherein each of the image processing parameter sets is a set of parameters used in a process of processing the ultrasound image; and processing, automatically by the at least one processor, the ultrasound image based on the target image processing parameter set.

* * * * *